(12) United States Patent
Hochman

(10) Patent No.: US 6,905,482 B2
(45) Date of Patent: *Jun. 14, 2005

(54) SAFETY IV CATHETER INFUSION DEVICE

(75) Inventor: Mark N. Hochman, Lake Success, NY (US)

(73) Assignee: Milestone Scientific, Inc., Livinston, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/742,312

(22) Filed: Dec. 18, 2003

(65) Prior Publication Data

US 2004/0186433 A1 Sep. 23, 2004

Related U.S. Application Data

(63) Continuation of application No. 10/174,246, filed on Jun. 18, 2002, now Pat. No. 6,726,658.

(51) Int. Cl.⁷ .......................... A61M 5/179; A61M 5/00; A61M 5/32
(52) U.S. Cl. ............. 604/164.08; 604/110; 604/164.12; 604/188; 604/198
(58) Field of Search ........................... 604/110, 164.01, 604/164.07, 164.08, 164.12, 165.01, 192, 194, 195–196, 198–199, 188; 128/919

(56) References Cited

U.S. PATENT DOCUMENTS

| | | | | | |
|---|---|---|---|---|---|
| 4,917,669 | A | * | 4/1990 | Bonaldo | 604/192 |
| 5,520,654 | A | * | 5/1996 | Wahlberg | 604/164.08 |
| 6,325,781 | B1 | * | 12/2001 | Takagi et al. | 604/198 |

* cited by examiner

Primary Examiner—Nicholas D. Lucchesi
Assistant Examiner—Catherine S. Williams
(74) Attorney, Agent, or Firm—Gottlieb Rackman & Reisman, P.C.

(57) ABSTRACT

A device for delivering an IV catheter to an IV infusion site is disclosed. The device includes a cylindrical housing adapted to fit into the hand of the clinician. A catheter assembly is disposed in the housing and can be advanced to an extended position and retracted. The catheter assembly includes a needle adapted to be inserted into the vein and the catheter is mounted on the needle to allow the catheter to be removed at will. The catheter assembly is rotated as the needle is inserted into the vein. Preferably the catheter assembly is rotated during the insertion of the needle and catheter. After the needle and catheter are inserted into the vein, the needle is retracted into the housing leaving the catheter in place. The housing and the needle can now be discarded.

22 Claims, 3 Drawing Sheets

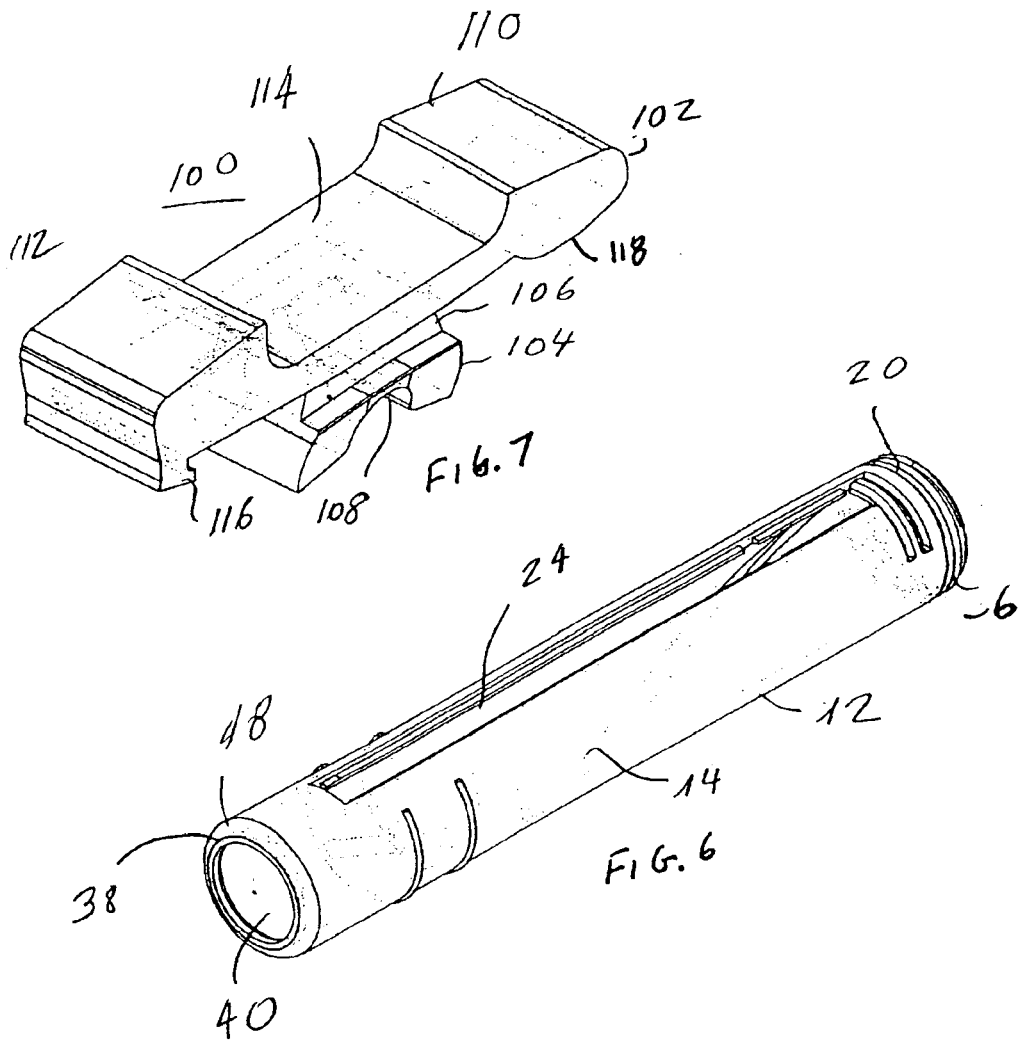

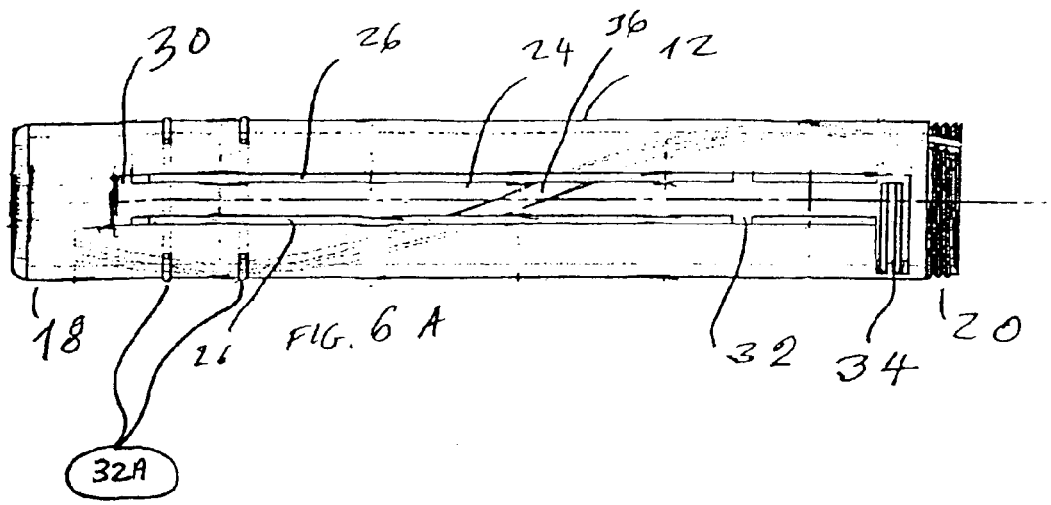
FIG. 6A
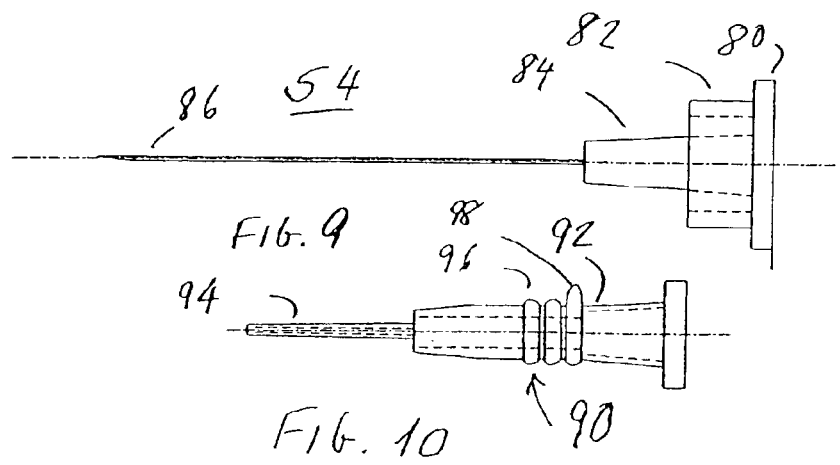
FIG. 9
FIG. 10

SAFETY IV CATHETER INFUSION DEVICE

RELATED APPLICATIONS

This application is a continuation to application Ser. No. 10/174,246 filed Jun. 18, 2002, now U.S. Pat. No. 6,726,658.

BACKGROUND OF THE INVENTION a. Field of Invention

This invention pertains to a device used to establish an IV catheter in a patient. More particularly, the invention pertains to a safety infusion device that includes a handpiece used to store and to selectively extend the IV catheter so that it can be introduced into the patient, the handpiece being constructed and arranged to insure that the IV catheter and the so-called underlying needle can be retracted into the barrel at will to protect clinicians from accidental needlesticks.

b. Description of the Prior Art

IV infusion is one of the most widely used procedures performed in hospitals and other healthcare provider sites. These infusions involve continuously injecting one or more liquids into the veins of a patient to achieve various results. Simple infusion systems may consist of a catheter inserted into the vein and secured to the patient, a pole holding a bottle or bag used as the source of the liquid, a flexible tube feeding the liquid to the catheter either directly, or though some kind of fluid control device. More complex devices include fusion pumps that can deliver fluids to the patient at carefully metered rates using specific profiles.

However, independent of which infusion system is used, the IV catheter must first be established. Many different devices are used to perform this step. A popular system consists of a cylindrical receptacle. A hollow steel needle is attached co-axially to one end of the receptacle. A hollow catheter is mounted on the steel needle in a coaxial arrangement. The hollow catheter has a shaft, preferably made of a plastic material and terminating in a standard connector, such as a male Luer lock. A spring is disposed in the receptacle so that when a latch mounted on the receptacle is activated, the steel needle separates from the catheter and is snapped into the receptacle. Once the steel needle is snapped into the receptacle, it is locked in place so that it cannot be extended and reused. Since the needle and the catheter are normally exposed, a protective cap is generally provided over the needle.

Using this type of system a catheter is established as follows. First, the clinician finds and preps a proper site on the skin. Next, the system is removed from a sealed enclosure, and its protective cap is removed. The needle and the catheter mounted thereon are inserted through the skin until the tip of the needle and the catheter reaches a predetermined site. The catheter is then secured with the forefinger of one hand and the latch is activated to cause the needle to snap into the receptacle before a needlestick. The receptacle with the captured needle is then disposed. Systems of this kind are available from Becton Dickinson of Franklin Lakes, N.J.; Johnson & Johnson Medical, Inc. of Arlington, Tex., and described in the following patents, incorporated herein by reference:

| | | | |
|---|---|---|---|
| 5,688,249 | 5,520,654 | 5,304,136 | 5,700,250 |
| 5,141,497 | 5,683,365 | 5,755,709 | D378,405 |
| 5,348,544 | 5,749,857 | 5,755,709 | 5,411,486 |
| 5,792,122 | 5,795,339 | 5,676,658 | D381,418 |
| 5,690,619 | | | |

However, these systems are not satisfactory for several reasons. As is well known in the art, the catheter has to extend into a vein and must be oriented properly in order for it to be effective. However, very often clinicians cannot find the proper vein or the proper infusion site on their first try. Therefore, after the needle and catheter have been inserted, the whole system becomes contaminated. Often, before the system can be reinserted, a new site has to be found and prepared.

The clinician, especially if she is alone, cannot select and prepare a new site while holding the contaminated system and therefore must make a decision on what to do with it. At least one manufacturer suggests that the system should be discarded. However, obviously, this is a wasteful step.

The clinician can also decide to recap the needle and then place it on a horizontal position. However, this process requires two hands and is exactly the situation that subjects people to inadvertent needlesticks.

Another disadvantage of existing systems is that they normally require a linear or translational motion of the needle during insertion. This is disadvantageous because it causes the needle to bend thereby causing pain to the patient. Moreover, if the needle bends during insertion, it will miss the vein and the process has to be repeated.

Commonly assigned application Ser. No. 09/506,484 filed Feb. 17, 2000, entitled HAND-PIECE FOR INJECTION DEVICE WITH A RETRACTABLE AND ROTATING NEEDLE, now U.S. Pat. No. 6,428,517 issued Aug. 6, 2002 and incorporated herein by reference, discloses an injection device with a barrel from which a needle is selectively extended and retracted using a translational and rotational motion for dispensing an anesthetic to a patient.

Commonly assigned patent application Ser. No. 09/745, 751 filed Dec. 21, 2000, entitled METHOD OF PERFORMING AN INJECTION USING A BI-DIRECTIONAL ROTATIONAL INSERTION TECHNIQUE, now 2001/ 10051,798 and incorporated herein by reference discloses the advantages of using a bi-directional rotational technique for dispensing anesthetics.

OBJECTIVES AND SUMMARY OF THE INVENTION

An objective of the present invention is to provide a system for establishing a catheter which overcomes the above-mentioned disadvantages.

A further objective is to provide a system that can be used easily by clinicians.

Other objectives and advantages will become apparent from the following description.

Briefly, the subject application pertains to a device for establishing an IV catheter by a clinician. The device includes a housing sized and shaped to fit in the hand of the clinician; a catheter assembly including a catheter member with a front portion adapted to be inserted into the vein of a patient; and a control member adapted to reciprocate the catheter assembly within said housing between a retracted position in which said catheter assembly is completely contained in said housing and an extended position in which said catheter member extends outwardly of said housing.

A catheter member can be removably attached to the catheter assembly so that it can be removed in the extended position.

The catheter assembly includes a needle member with a needle extending outwardly of the housing when the catheter member is in the extended position. The needle is arranged and constructed for insertion in the vein with the catheter member being telescopically associated with the needle member. The catheter member is removably attached to the needle member.

In one embodiment the catheter member and the housing cooperate to rotate the catheter assembly about a longitudinal axis as the catheter assembly is reciprocated by said control member.

The device also can include locking means for locking the catheter assembly or the needle after the catheter replacement with respect to the housing. These locking means can be adapted to lock the catheter assembly in either the retracted position or the extended position. In addition, the control member can be disabled by the use of the same, or a different locking means so that after the catheter element is properly established, the needle used to establish the catheter cannot be reused.

BRIEF DESCRIPTION OF THE DRAWINGS

FIG. 6 shows an orthogonal view of a barrel for the device of FIG. 1;

FIG. 6A shows a plan view of a barrel for the device of FIG. 1;

FIG. 7 shows an orthogonal view of a control button;

FIG. 8 shows an orthogonal view of the piston for the device of FIG. 1;

FIG. 9 shows a side view of the needle member for the device of FIG. 1; and

FIG. 10 shows a side view of the catheter for the device of FIG. 1.

DETAILED DESCRIPTION OF THE INVENTION

Figure 1:
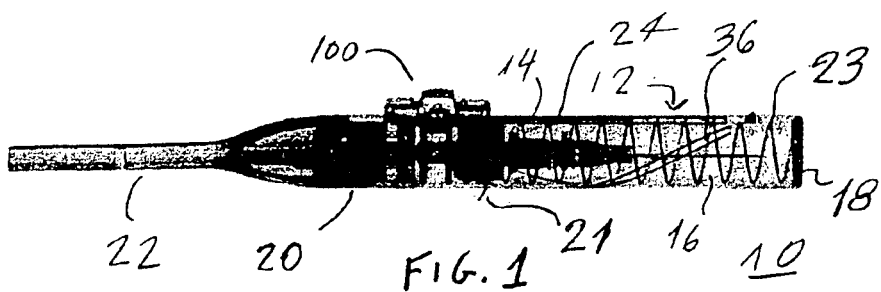
FIG. 1 shows a sectional side view of a device in a retracted position constructed in accordance with this invention.

Referring now to the Figures, a device 10 constructed in accordance with this invention consists of a cylindrical housing or barrel 12 having an outer surface 14, an inner surface 16, a front end 18 and a rear end 20. An end piece 22 is attached to the rear end 20 of the barrel. The barrel 12 defines a cylindrical housing.

As shown in FIG. 1, a catheter assembly 21 is provided in the barrel 12. This catheter assembly is biased toward a retracted position by a biasing means such as a coil spring 23.

FIGS. 6 and 6A show more details of the barrel 12. It includes a longitudinal slot 24. The slot 24 is formed with two ledges 26 extending along the sides of the slot 24. These ledges terminate at a gap near the front end 18 to define a front key 28. In addition, gaps in the ledges 26 near the rear end 20 define a rear key 32. Two radial ribs 32A form an outer surface 14 of the barrel 12 to provide a better grip. At the rear end of the slot 24 a portion of the barrel is cut to form an arcuate tongue 34. The purpose of this tongue 34 is described in more detail below. The barrel is preferably made of a plastic material and is preferably transparent so that the clinician can see its contents. For example, the barrel could be made of an acrylic-based multipolymer such as Cyrolite #GS-90.

As seen in FIG. 1, the inside surface 16 of the barrel 12 is formed with a helical groove 36. The rear end 20 is threaded. The front end 18 is formed with an annular end wall 38 with an orifice 40.

The catheter assembly 21 consists of a piston 50 shown in detail in FIG. 8, a catheter member 52 and a needle member 54. The piston is formed of an axle 56 supporting a rear hub 58, a center hub 60 and a front hub 62. The rear and front hubs 58, 62 have approximately the same radial dimension and they are sized to allow the piston 50 to fit into the barrel 12 with the hubs 58, 62 slidingly engaging the inner surface 16. The axial spacing between the two hubs is sufficient to stabilize the piston 50 and the elements attached thereto (and described below) as they reciprocate through the barrel 12. The center hub 60 has a smaller diameter and a somewhat curved cross section. The circumferential surface of hub 62 is optionally provided with a knob 64 which is sized and shaped to fit into helical groove 36. Therefore, as the piston 50 is reciprocated through the barrel, it is also rotated about its longitudinal axis by the caming action on the knob 64 as it travels through groove 36.

Hub 62 also includes a tubular wall 66 disposed about an end portion 68 of axle 56. The inner surface of the tubular wall 66 is formed with a helical groove 70. The wall 66 and the end portion 68 cooperate to define a female Luer lock 72.

Details of the needle member 54 are shown in FIG. 9. It includes a disk 80, a cylindrical body 82, a frustoconical extension 84 and a hollow steel needle 86. These elements are attached to each other as shown. The disk 80 is sized and shaped so that it can be introduced into the Luer lock 72. In this manner, the needle member 54 is firmly attached to the piston 50. The needle member 54 can be secured to the piston 50 by other means as well, for example, by using an adhesive.

Figure 3:
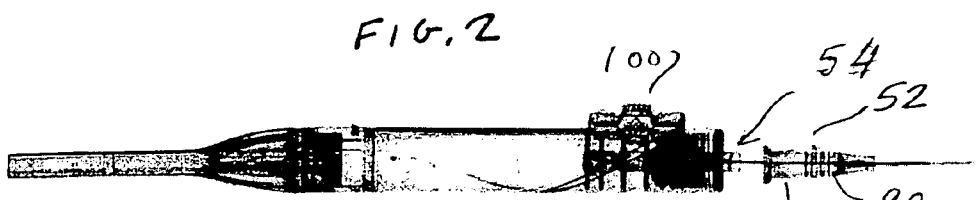
FIG. 3 shows a sectional side view of the device of FIG. 1 in the extended position with the catheter partly removed.

As best seen in FIGS. 3 and 10, the catheter member 52 is formed with a hollow substantially cylindrical body 90 with a rear portion 92 which has a relatively large diameter. The body 90 also has a front portion 94 which is much thinner than the rest of the body 90. The body 90 also includes several circumferential ribs 96 forming a grip for the catheter. A portion of one of the ribs is extended radially to form a tab 98.

The catheter member 52 is made of a flexible plastic material. Preferably catheter member 52 is somewhat translucent.

Figure 2:
FIG. 2 shows a sectional side view of the device of FIG. 1 in the extended position.

The catheter member 52 and the needle member 54 are sized and shaped so that the catheter member 52 fits over the needle member 54 as shown in FIG. 2 with the steel needle 86 extending through and beyond the front portion 94. Moreover, the rear portion 92 is sized to form an interference fit with the extension 84. The catheter member 52 is freely removable by a clinician from the needle member 54. Of course, there is sufficient interference fit provided to insure that the catheter member 54 does not separate easily from the needle member without substantial force applied thereto. This force may be applied to tab 98 as explained in more detail below.

Finally, the device 10 includes a control member or control means 100 shown in more detail in FIG. 7. The control member 100 is formed of an upper body 102, a lower body 104 and an intermediate portion 106. The lower body 104 is formed with an arcuate surface 108 designed to conform to the shape of the hub 60 on piston 50. The upper body 102 is formed with two wings 110, 112 and a depression 114 defined therebetween. The depression 114 is sized and shaped to accommodate the finger of a clinician. The wing 112 is formed with a tab 116 extending downwardly and is sized and shaped to fit into the keys 30 and 32 on barrel 12. The control member 100 is made of a plastic material.

The control member 100 is sized and shaped to fit into the slot 24 with the upper body 102 disposed outside the barrel 12 and riding on the ledges 26 and the lower body 104 being disposed inside the barrel with the hub 60 being captured by curved surface 108.

The device 10 is assembled by attaching the catheter member 52 to the needle element 54 and attaching the needle element to the piston 50, thereby completing the catheter assembly 21. The spring 23 and catheter assembly 21 are then inserted through a hole (not shown) in the rear end 20 of barrel 12. The control member 100 is also mounted on the barrel 12. Next, the end piece 22 is attached thereto by screwing the same over the threads of the rear end. Preferably an adhesive is also used to insure that the end piece 22 does not separate from the barrel. Alternatively, the end piece 22 is attached to the barrel 12 without any threading action. Once the end piece is installed, the elements described above are captured by the barrel (except for the catheter member 52) and cannot be removed without breakage.

Initially the elements of the device 10 are arranged in a closed or retracted position as shown in FIG. 1. Spring 23 has a diameter which is slightly larger than the diameter of wall 66. In this retracted position, the spring 23 is expanded and applies a biasing force between the end wall 38 of the barrel 12 and the wall 66 on piston 50. The control member 100 is positioned over the piston 50 with the hub 60 being captured by the curved surface 108.

The control member 100 is formed so that its tab 116 extends downwardly in the rear key 32 of slot 26. Moreover the control member 100 is formed and arranged so that as the control member 100 is shifted to the right to the retracted position, a bottom wail 118 of wing 110 (shown in FIG. 7) comes into contact with the end of tongue 34. The tongue 34, being slightly higher, and in effect pushes the wing 110 slightly upward as well. As a result, the opposite wing 112 with the tab 116 is pushed downward into the key 30. In this manner the control member 100 and the catheter assembly 21 is locked into the retracted position by the locking means formed by the cooperation between the control member 100 and key 32. The device 10 is sealed in a suitable package (not shown) and stored in this position.

The device 10 is used to establish the catheter member 52 as follows. Typically, an infusion procedure is initiated by a clinician by selecting and prepping the infusion site. The clinician then removes the device 10 from its package and holds it in a pinching grip. In this grip the thumb is positioned on the control member 100, and the remaining fingers being wrapped around the barrel to stabilize it. The device 10 is sized and shaped so that in this pinching grip, the pinky finger wraps around the end piece 22.

The clinician then pushes on the wing 110 axially inward causing the top body to twist slightly radially inward, and lift the tab 116 out of rear key 32. This action unlocks the control member 100. Next, the clinician advances the control member 100 slightly forward. Because the surface 108 captures the hub 60, this movement forces the whole catheter assembly 21 to move forward as well. The clinician continues the translation of the control member 100 forward until a portion of the needle 96 extends through the hole 40 (FIG. 6).

Next, the clinician positions the device 10 next to the infusion site with the tip of the needle 86 resting against the skin. The clinician then continues to advance the control member 100 until it reaches the front key 30. The clinician can lock the control member 100 and the catheter 21 by pushing the wing 112 inwardly thereby causing the tab 112 to pivot counterclockwise and engage front key 30. In this position, a portion of needle member 54 and most of the catheter member 52 extend out of the barrel 12 as shown in FIG. 2. This position is the extended position of the device and the control member 100 and front key 30 provide a locking means for locking the catheter assembly in the extended position.

It should be appreciated that as the control member 100 is advanced from the rear key 32 to the front key 30 in a translational motion through the slot 26, because of the caming action between the knob 64 and spiral groove 36, the catheter assembly 21 is translated forward as well from the retracted to the extended position, and is simultaneously rotated about its longitudinal axis and the longitudinal axis of the barrel 12. Thus, the knob 64 and spiral groove 36 provide a means of rotating the catheter assembly 21. As explained in the above-identified application Ser. No. 09/506,484 filed Feb. 17, 2000, and in application Ser. No. 09/745,751 filed Dec. 21, 2000, this combined or bidirectional motion is very advantageous because as the needle 86 penetrates the skin and the tissues and advances to the vein, its simultaneous rotation insures that the patient suffers less pain. In addition, it prevents the needle 86 from bending and insures that the needle advances precisely in the direction and to the location desired by the clinician.

The needle 86 must be advanced sufficiently so that the front portion 94 is in fluid communication with the vein as well. The front portion 94 is thin enough so that it slips easily through the sidewalls of the vein. As discussed above, needle 86 is hollow and has an opening at its tip. A second opening may be provided on the needle 86 under the front end 94. When the needle 86 and front end 84 are inserted into the vein, blood from the vein flows into the needle 86 and oozes out of this second opening, under the front end 94. Since the catheter 52 is translucent, this blood is easily visible to the clinician. Moreover, since the needle 86 is hollow, some of the blood also flows back in the housing where it becomes visible as well. This provides confirmation that the needle 86 and the catheter member 52 are properly positioned in the vein.

If for any reason the clinician has to move to a different infusion site, he can withdraw the needle from the patient. If this motion occurs before the control member 100 reached front key 30 then the clinician can merely release the control member 100 and the catheter assembly 21 is then automatically returned to the retracted position by the spring 23. If this motion is desired after the front key 30 is reached, then the clinician must first unlock the control member from the front key by pressing inwardly on wing 110.

Once the catheter assembly 21 is returned to its retrieved position, the device 10 can be rested on a flat surface and the clinician can go on with other tasks (such as prepping the new site) without fear of needlesticks even if the needle 86 has been contaminated.

After the needle 86 and the catheter member 52 are properly positioned in the vein, the needle 86 is withdrawn as follows. The clinician shifts his forefinger to rest on the front end 94 of the catheter member 52. The rest of his fingers are still wrapped around the barrel 12. In this position, the clinician unlocks the control member 100 as discussed above and releases it. The spring 23 forces the needle member 54 to withdraw telescopically and separate from the catheter 52. The needle member 54 and the piston 50 are then snapped back to the retracted position. During this motion, the clinician holds the catheter member 52 in place (i.e., inserted in the vein). Thus, the clinician needs to use only a single hand from the beginning of the process until the catheter member 54 is established in the vein and is separated from device 10. As explained above, in prior art devices this same operation requires the use of two hands.

FIG. 3 shows the catheter member 52 being removed from the needle member 54.

Figure 4:
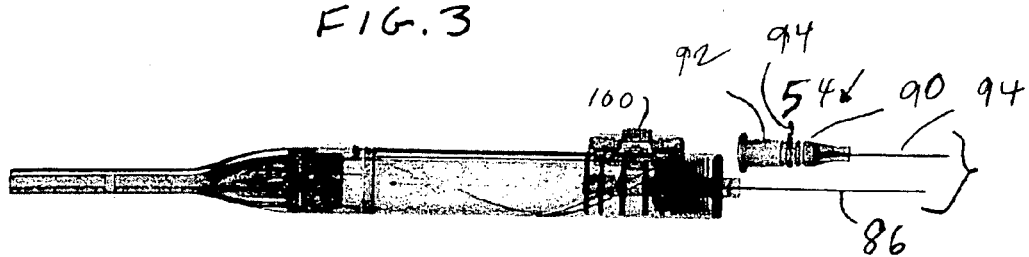
FIG. 4 shows a sectional side view of the device of FIG. 1 in the extended position with the catheter completely removed.

FIG. 4 shows the catheter member 52 being separated from the rest of the device 10.

Figure 5:
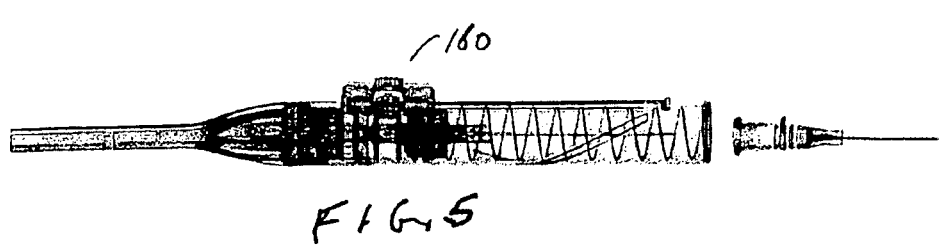
FIG. 5 shows a sectional side view of the device of FIG. 1 with the needle retracted and the catheter removed.

FIG. 5 shows the catheter assembly 21 without the catheter member 52 in the retracted position.

Once the device 10 is in the retracted position of FIG. 5, it can be disposed. The catheter member 52 can be connected to a standard IV tube by attaching to a standard Luer lock, or by using other well known means.

Importantly, in many instances the clinician may want to insure that once its catheter member 54 has been properly established, the device 10 is not reused in any way and that the needle member 54 stays in the retracted position. This is accomplished by providing a control disabling means for the device which insures that the control member 100 is inoperative and cannot be used to advance the needle. This disabling means can be implemented by making the intermediate portion 106 of the control member 100 frangible. Then, once the catheter member 52 is properly established in the vein, the top body 102 is broken off from the bottom body 104. Once this step is completed, the piston 50 and the needle member 54 are trapped inside the barrel 12 and cannot be removed without breaking the barrel.

The device may be used in a different manner as well. For example, if the clinician does not want to take advantage of the simultaneous translation and rotation of the needle member 54, he can advance the catheter assembly 21 from the retracted to the extended position first, and then with the needle member being fully extended, he can start inserting the needle 86 through the skin toward the selected vein. For this type of operation, since the rotation of the needle 86 is not required, the knob 64 and the groove 26 may be omitted.

Other modifications may be made to the device 10 as well. For example, the means for locking the control member 100 either in the retracted position, the extended position, or both, may be omitted.

While the invention has been described with reference to several particular embodiments, it is to be understood that these embodiments are merely illustrative of the principles of the invention. Accordingly, the embodiments described in particular should be considered as exemplary, not limiting, with respect to the following claims.

I claim:

1. A device for establishing an IV catheter by a clinician comprising:
    a housing sized and shaped to fit in the hand of the clinician;
    a catheter assembly including a catheter member with a front portion adapted to be inserted into the vein of a patient;
    a control member adapted to reciprocate said catheter assembly within said housing between a retracted position in which said catheter assembly is completely contained in said housing and an extended position in which said catheter member extends outwardly of said housing, said control member being movable with respect to said catheter assembly for selectively locking said catheter assembly with respect to said housing; and
    rotating means adapted to rotate said catheter assembly about an axis as said catheter assembly is reciprocated by said control means.

2. The device of claim 1 wherein said catheter member is removably attached to said catheter assembly so that it can be removed in said extended position.

3. The device of claim 1 wherein said catheter assembly indudes a needle member including a needle which extends outwardly of said housing when said catheter member is in the extended position, said needle being arranged and constructed for insertion in the vein, said catheter member being telescopically associated with said needle member.

4. The device of claim 3 wherein said catheter member is removably attached to said needle member.

5. The device of claim 1 wherein said catheter member and said housing cooperate to rotate said catheter assembly about a longitudinal axis as said catheter assembly is reciprocated by said control member.

6. The device of claim 1 further comprising locking means for locking said catheter assembly with respect to said housing.

7. The device of claim 6 wherein said locking means is adapted to lock said catheter assembly in said retracted position.

8. The device of claim 6 wherein said locking means is adapted to lock said catheter assembly in said extended position.

9. The device of claim 1 further comprising disabling means adapted to selectively disable said catheter assembly within said housing to prevent said catheter assembly for being moved extend outside said housing.

10. A device adapted to establish a catheter for providing IV infusions to a patient through a vein, said device comprising:
    a cylindrical housing having a front end, a rear end and a cylindrical surface extending therebetween;
    a catheter assembly including a needle member with a needle and a catheter member removably attached to said needle member and telescopically arranged on said needle;
    control means for reciprocating said catheter assembly between a retracted position wherein said catheter assembly is completely disposed within said cylindrical and an extended position wherein said needle and said catheter member are operative to be inserted in the vein, said control means and said catheter assembly being rotatably joined to allow said catheter assembly to rotate with respect to said housing during said reciprocating; and
    rotating means adapted to rotate said catheter assembly about an axis as said catheter assembly is reciprocated by said control means.

11. The device of claim 10 wherein said catheter assembly further comprises a piston, said needle member and said catheter member being connected to said piston.

12. The device of claim 10 further comprising a first locking means for locking said catheter assembly in said retracted position.

13. The device of claim 10 further comprising a second locking means for locking said catheter assembly in said extended position.

14. The device of claim 10 further comprising control disabling means adapted to disable said control means to prevent said catheter assembly from being moved to extend outside said cylindrical housing.

15. The device of claim 10 further comprising biasing means for biasing said catheter assembly toward said retracted position.

16. The device of claim 1 wherein said housing and said control member cooperate to lock said catheter assembly in a retracted position in which said catheter is disposed within said housing.

17. The device of claim 1 wherein said housing and said control member cooperate to lock said catheter assembly in an extended position in which said catheter extends outwardly of said housing.

18. The device of claim 1 wherein said housing includes at least a hole and said control member is pivoting with respect to said housing and said catheter assembly between two positions, including a first position in which said control member engages said hole, and a second position that allows the catheter assembly to be reciprocated within said housing.

19. A device for establishing an IV catheter by a clinician comprising:
- a housing sized and shaped to fit in the hand of the clinician:
- a catheter assembly including a catheter member with a front portion adapted to be inserted into the vein of a patient;
- a control member adapted to reciprocate said catheter assembly within said housing between a retracted position in which said catheter assembly is completely contained in said housing and an extended position in which said catheter member extends outwardly of said housing; and
- control disabling means adapted to disable said control means to prevent said catheter assembly from being moved to extend outside said housing.

20. A device adapted to establish a catheter for providing IV infusions to a patient through a vein, said device comprising:
- a cylindrical housing having a front end, a rear end and a cylindrical surface extending therebetween;
- a catheter assembly including a needle member with a needle and a catheter member removably attached to said needle member and telescopically arranged on said needle;
- control means for reciprocating said catheter assembly between a retracted position wherein said catheter assembly is completely disposed within said cylindrical and an extended position wherein said needle and said catheter member are operative to be inserted in the vein; and
- control disabling means adapted to disable said control means to prevent said catheter assembly from being moved to extend outside said housing.

21. A device for establishing an IV catheter by a clinician comprising:
- a housing sized and shaped to fit in the hand of the clinician;
- a catheter assembly including a catheter member with a front portion adapted to be inserted into the vein of a patient;
- a control member adapted to reciprocate said catheter assembly within said housing between a retracted position in which said catheter assembly is completely contained in said housing and an extended position in which said catheter member extends outwardly of said housing, said control member being movable with respect to said catheter assembly with respect to said catheter assembly for selectively locking said catheter assembly with respect to said housing; and
- control disabling means adapted to disable said control means to prevent said catheter assembly from being moved to extend outside said housing.

22. A device adapted to establish a catheter for providing IV infusions to a patient through a vein, said device comprising:
- a cylindrical housing having a front end, a rear end and a cylindrical surface extending therebetween;
- a catheter assembly including a needle member with a needle and a catheter member removably attached to said needle member and telescopically arranged on said needle;
- control means for reciprocating said catheter assembly between a retracted position wherein said catheter assembly is completely disposed within said cylindrical and an extended position wherein said needle and said catheter member are operative to be inserted in the vein, said control means and said catheter assembly being rotatably joined to allow said catheter assembly to rotate with respect to said housing during said reciprocating; and control disabling means adapted to disable said control means to prevent said catheter assembly from being moved to extend outside said cylindrical housing.

* * * * *